United States Patent [19]

Rutter et al.

[11] 4,292,069
[45] Sep. 29, 1981

[54] ARYLTHIOUREIDO PYRIDINECARBAMINO COMPOUNDS AND USE AS PLANT GROWTH REGULANTS

[75] Inventors: Jerry L. Rutter; Charles G. Gibbs, both of Shawnee Mission; Loren W. Hedrich, Overland Park, all of Kans.

[73] Assignee: Gulf Oil Corporation, Pittsburgh, Pa.

[21] Appl. No.: 227,825

[22] Filed: Jan. 23, 1981

Related U.S. Application Data

[62] Division of Ser. No. 101,654, Dec. 10, 1979.

[51] Int. Cl.$^3$ .............................................. A01N 43/40
[52] U.S. Cl. ............................................ 71/94; 71/76
[58] Field of Search .................................... 71/94, 76

[56] References Cited

U.S. PATENT DOCUMENTS

| | | | |
|---|---|---|---|
| 3,712,914 | 1/1973 | Tilles | 71/94 X |
| 4,137,067 | 1/1979 | Gatzi | 71/94 |
| 4,193,788 | 3/1980 | Shudo et al. | 71/94 |

Primary Examiner—Catherine L. Mills
Attorney, Agent, or Firm—Carl A. Cline

[57] ABSTRACT

A method of regulating the growth of plants, including combating unwanted vegetation, comprises applying to the plants, either on seed, the soil or directly on the plants an effective amount of a novel compound of the class having the general structural formula

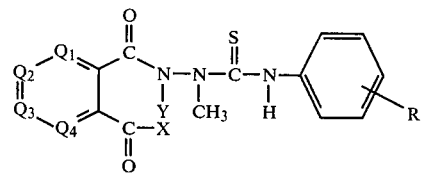

in which one of $Q_1$, $Q_2$, $Q_3$ or $Q_4$ is N,
X is —OH or —O—($C_1$-$C_4$ alkyl) and Y is H or X and Y together represent a bond between carbon and nitrogen atoms and R is H or one or two of the following substituents: —Br, —Cl, —F, —I, —CF$_3$, —CH$_3$, —NO$_2$ or —C≡N, or an agriculturally acceptable salt thereof.

42 Claims, No Drawings

ARYLTHIOUREIDO PYRIDINECARBAMINO COMPOUNDS AND USE AS PLANT GROWTH REGULANTS

This is a division of application Ser. No. 101,654 filed Dec. 10, 1979.

DESCRIPTION OF THE INVENTION

Many chemical substances have been found to have growth regulating effects on plants. Change of shape of plants, crinkling and folding of leaves, stunting of growth, defoliation, stimulation of root growth on cuttings and other effects are frequently observed. It is usually necessary to apply growth regulating substances to plants at comparatively low rates in order to have the growth regulating effects clearly evident. At higher rates a selective kill of vegetation is usually obtained, as some species of plants are effected more than others. Growth regulants have, in fact been used more as selective herbicides than for other purposes because in many instances the growth regulating effects exhibited by these substances have no other practical utility. However, a class of growth regulant compounds has now been discovered that produces a number of useful effects, differing from one plant species to another. For example, some of these compounds promote tillering (branching at the base of the plant) in oats and other grains and increase of fruit set in certain other plants.

Briefly, the class of growth regulant compounds has the general structural formula

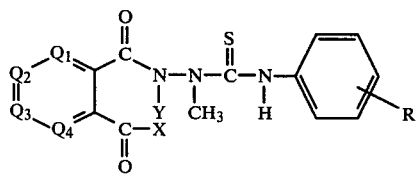

in which one of $Q_1$, $Q_2$, $Q_3$ or $Q_4$ is N, X is —OH or —O—($C_1$-$C_4$ alkyl) and Y is H or X and Y together represent a bond between carbon and nitrogen atoms and R is H or one or two of the following substituents: —Br, —Cl, —F, —I, —$CF_3$, —$NO_2$ or —C≡N, including agriculturally acceptable salts thereof. Acceptable salts include amine salts and metallic salts of a carboxy substituent, as well as salts with the basic heterocyclic nitrogen atom and isothuronium salts. It will be understood that salts which leave toxic heavy metal residues are not agriculturally acceptable.

Synthesis of the Growth Regulants

The growth regulants may be synthesized according to the following general scheme:

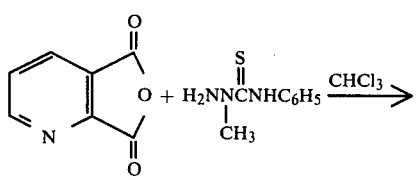

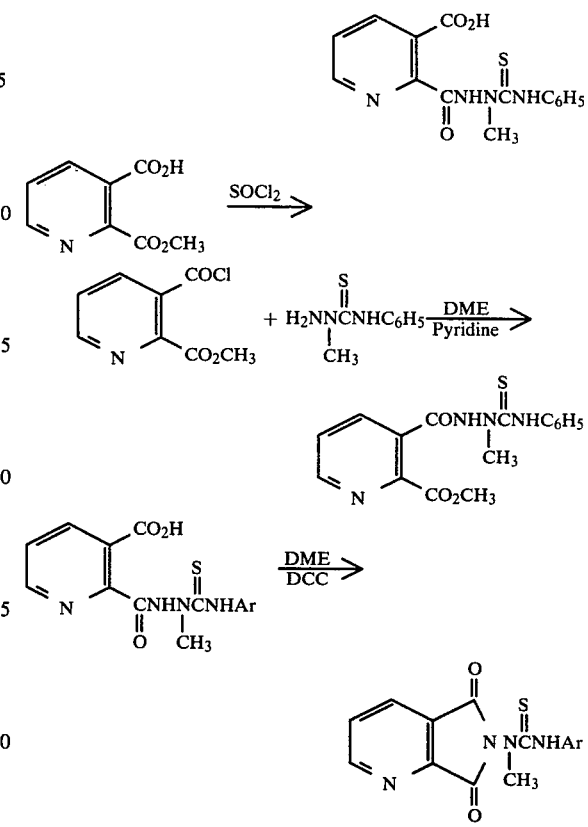

Below are specific illustrative procedures.

(All temperatures in the following procedures are °C.)

Preparation of 1-(3'-Carboxy-2'-pyridinecarbonyl)-2-methyl-4-phenyl-3-thiosemicarbazide To a suspension of 4.5 g (0.03 mole) of pyridine-2,3-dicarboxylic anhydride in 100 ml chloroform was added 5.4 g (0.03 mole) of 2-methyl-4-phenyl-3-thiosemicarbazide. The resulting reaction mixture was allowed to stir at room temperature overnight. After filtering and drying there was obtained 9.3 g of the desired product, mp: 152°–153°. The IR and NMR spectra were consistent with the proposed structure.

Preparation of 1-(2'-Carbomethoxy-3'-pyridinecarbonyl)-2-methyl-4-phenyl-3-thiosemicarbazide A suspension of 4.5 g (0.025 mole) of 2-carbomethoxy-3-pyridine carboxylic acid in 75 ml of thionyl chloride containing a few drops of dimethylformamide was refluxed until solution occurred. Evaporation gave 4.9 g of a brown oil consisting of crude ester-acid chloride which was used without further purification.

To a solution of 4.4 g (0.0245 mole) of 2-methyl-4-phenyl-thiosemicarbazide in 50 ml of dimethoxyethane containing 2.0 g (0.0245 mole) of pyridine cooled in −35° was added dropwise a solution of the above ester-acid chloride dissolved in 25 ml of dimethoxyethane. After complete addition the reaction mixture was allowed to come to room temperature and stirred overnight. The reaction mixture was then added to ice water and extracted with ethyl acetate. The organic layer was dried and evaporated to give a gummy residue which was crystallized from ether-ethyl acetate. There was obtained 3.2 g of the desired product, mp: 128°–129°. The IR and NMR spectra were consistent with the proposed structure.

Preparation of
N-(1-Methyl-3-phenylthioureido)-2,3-pyridine-carboximide

To a suspension of 6.6 g (0.02 mole) of 1-(3′-carboxy-2′-pyridinecarbonyl)-2-methyl-4-phenyl-3-thiosemicarbazide in 150 ml of dimethoxyethane was added dropwise 4.1 g (0.02 mole) of dicyclohexylcarbodiimide in 50 ml of dimethoxyethane. The resulting yellow solution was allowed to stir at room temperature overnight. The precipitated dicyclohexylurea was removed by filtration and the yellow filtrate was evaporated almost to dryness. Isolation of the solid gave 2.3 g of the desired product, mp: 207°–210°. The IR and NMR were consistent with the proposed structure.

In the following table there are listed novel compounds which have been made by means of the general procedures which are illustrated above.

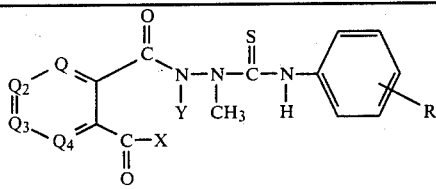

| Compound No. | Q | X | Y | R | mp (°C.) |
|---|---|---|---|---|---|
| 4167 | $Q_1 = N$ | —OH | —H | 2-F | 152–153 |
| 4166 | | | | 4-CH$_3$ | 148–149 |
| 4165 | | | | 3-Br | 143–145 |
| 4051 | | | | 4-Cl | 154–156 |
| 4004 | | | | 3,4-di Cl | 157–159 |
| 4003 | | | | 3-CH$_3$ | 152–154 |
| 4002 | | | | 2,4-dimethyl | 149–154 |
| 4001 | | | | 3,4-dimethyl | 155–161 |
| 3999 | | | | 3-Cl | 143–144 |
| 3998 | | | | 4-CH$_3$ | 165–168 |
| 3997 | | | | 3-CF$_3$ | 141–142 |
| 3996 | | | | 3,5-di Cl | 156–157 |
| 3970 | | | | 4-NO$_2$ | 152–156 |
| 3925 | | | | 4-F | 143–145 |
| 3924 | | | | 3-Cl-2-CH$_3$ | 149–150 |
| 3923 | | | | 2-Cl | 150–151 |
| 4228 | | | | 4-C≡N | 165–168 |
| 4227 | | | | 2,4-di Cl | 139–141 |
| 4226 | | | | 4-Br | 144–147 |
| 4225 | | | | 4-I | 148–149 |
| 3595 | | | | H | 149–151 |
| 4170 | $Q_1 = N$ | X+Y is C—N bond | | 2-F | 147–154 |
| 4169 | | | | 4-CF$_3$ | 173–177 |
| 4168 | | | | 3-Br | 156–162 |
| 4164 | | | | 3,4-di Cl | 162–165 |
| 4163 | | | | 3-CH$_3$ | 175–182 |
| 4162 | | | | 3,4-dimethyl | 142–151 |
| 4157 | | | | 3-Cl | gum |
| 4156 | | | | 4-CH$_3$ | 148–159 |
| 4155 | | | | 3-CH$_3$ | gum |
| 4154 | | | | 3,5-di Cl | 178–184 |
| 4148 | | | | 4-NO$_2$ | 198–203 |
| 4147 | | | | 3-Cl—2-CH$_3$ | gum |
| 4146 | | | | 2-Cl | gum |
| 4106 | | | | 4-F | 172–176 |
| 4096 | $Q_4 = N$ | —OCH$_3$ | —H | 4-F | 142–145 |
| 4095 | | | | 3-Cl | 103–111 |
| 4094 | | | | 4-CH$_3$ | 96–102 |
| 4093 | | | | 3-CF$_3$ | 111–114 |
| 4092 | | | | 3,5-di Cl | 159–161 |
| 4091 | | | | 3,4-di Cl | gum |
| 4090 | | | | 3-CH$_3$ | gum |
| 4089 | | | | 2,4-dimethyl | 72–86 |
| 4088 | | | | 3,4-dimethyl | 65–78 |

-continued

| Compound No. | Q | X | Y | R | mp (°C.) |
|---|---|---|---|---|---|
| 3817 | | | | —H | 128–129 |
| 3968 | $Q_1 = N$ | —OH | —H | 2-CH$_3$ | 159–160 |
| 3969 | | | | 3-F | 148–153 |
| 3984 | | | | —H | 148–151 |
| 4149 | | X+Y is C—N bond | | —H | 172–175 |
| 3600 | $Q_3 = N$ | —OH | —H | —H | 200 (dec) |
| 3818 | $Q_2 = N$ | —OCH$_3$ | —H | —H | 162–169 |
| 3848 | $Q_2 = N$ | X+Y is C—N bond | | —H | gum |
| 4098 | $Q_4 = N$ | —OCH$_3$ | —H | —H | 106–115 |

Use of the Growth Regulants

By application of an effective amount of the growth regulants, either pre- or post-emergently, various effects on young plants become apparent. These effects may be demonstrated by means of the following illustrative procedures.

Pre-emergent Application

Disposable paper trays about 2½ inches deep which were filled with soil were sprayed with aqueous spray mixtures at a rate of 10 lb. of active chemical per acre of sprayed area, then were seeded with 6 species of plant seeds and were covered with about ¼ inch of soil. The spray mixtures were prepared by dissolving the proper amount of growth regulant compound in 15 ml of acetone, adding 4 ml of a solvent-emulsifier mixture consisting of 60 wt. percent of a commercial polyoxyethylated vegetable oil emulsifier (96 wt. percent active ingredient, Emulphor EL-719), 20 wt. percent xylene and 20 wt. percent deodorized kerosene, then bringing total volume up to 60 ml by addition of warm water. Twenty-one days after seeding and treatment the plantings were examined and plant injury was rated according to the following schedule.

DEGREE OF EFFECT

0=no effect
1=slight effect, plants recovered
2=moderate effect, injury to 26 to 75 percent
3=severe effect, injury to 76 to 99 percent of foliage
4=maximum effect (all plants died)

Post-emergent Application

Several species of plants were grown in potting soil in disposable styrofoam trays and tomatoes were grown in four-inch pots in the greenhouse. Aqueous spray formulations were prepared and the growing plants were sprayed at a spray volume of 60 gallons per acre and an application rate of 5 lb. per acre. Spray mixtures were prepared in the manner described above. For comparative purposes, plants were also sprayed at 60 gal. per acre with a spray mixture containing no growth regulant. Plant injury was again rated according to the schedule disclosed above.

Observations of growth regulant effects in both pre- and post-emergent tests were observed and recorded as follows:

| Effect | Abbreviation in Tables |
|---|---|
| Formative effect on new growth | F |
| Epinasty | E |
| Growth reduction | G |
| Necrosis | N |
| Non-emergence | K |
| Chlorosis | C |

In the table below there are tabulated various observations of pre- and post-emergent herbicidal and growth regulant effects of the compounds disclosed above.

EFFECTS OF COMPOUNDS ON PLANT LIFE

| Compound No. | Pre-emergent Effects | | | | | | Post-emergent Effects | | | | | | Comments |
|---|---|---|---|---|---|---|---|---|---|---|---|---|---|
| | Digitaria sanguinalis | Celosia plumosa | Bromus inermis | Setaria italica | Raphanus sativus | Beta vulgaris | Setaria italica | Medicago sativa | Avena sativa | Raphanus sativus | Beta vulgaris | Lycopersicum esculentum | |
| 3595 | G1 | K1G1 | F3G2 | G2 | F1 | F2G1 | G2 | F2G1 | G1 | 0 | F2G2 | F2 | Increases fruit set |
| 3600 | F2G2 | F2G1 | F3G3 | F1 | F2G1 | F2G1 | 0 | F2G1 | G1 | 0 | F2G1 | F2 | " |
| 3817 | 0 | F2 | F2 | 0 | 0 | F1 | G1 | F1 | 0 | F1 | F2G1 | F2 | " |
| 3818 | F1 | F2G1 | F3G3 | F2G2 | F3G3 | K4 | G2F1 | F3G2 | F1G1 | F3G2 | F3G2 | F2 | " |
| 3848 | F1 | F2G1 | F3G2 | F2G1 | F1G1 | F3G1 | G2 | F3G1 | G1 | G2F1 | F3G2 | F2 | |
| 3923 | 0 | F1 | K2 | 0 | 0 | F1 | 0 | F1 | 0 | 0 | F2 | F1 | |
| 3924 | 0 | N4 | K3 | G2F1 | 0 | N4 | 0 | F2G1 | 0 | F1 | F3G1 | F1 | Increases fruit set |
| 3925 | G1 | F1 | K2F2 | 0 | F1 | F2 | F1 | F2 | F1 | F2G1 | F3G1 | F3 | Promotes tillering |
| 3968 | 0 | 0 | 0 | 0 | 0 | 0 | 0 | 0 | 0 | 0 | F1 | F3 | |
| 3969 | 0 | N2 | K2 | 0 | 0 | 0 | 0 | 0 | 0 | 0 | 0 | F1 | |
| 3970 | 0 | 0 | 0 | 0 | 0 | 0 | 0 | 0 | 0 | 0 | F1 | 0 | |
| 3996 | 0 | 0 | F2 | F1G1 | F1 | F2G1 | G1F1 | F1G1 | F1 | F1G1 | F3G3 | F3G3 | Increases fruit set |
| 3997 | 0 | F1G1 | F2 | F1 | F1 | F2G1 | N1 | F3G2 | F1G1 | F2 | F3G2 | F3G3 | |
| 3998 | F1 | F1 | F3G1 | F2G1 | F1 | F2G1 | F2G1 | F3G3 | G1 | F1 | F3G2 | F3G3 | |
| 3999 | F1G1 | F2G1 | F3G3 | F2G2 | F1 | F2G1 | F1G1 | F1 | F1G2 | F2G1 | F2G1 | F3 | |
| 4001 | C1G1 | | F2 | F1 | 0 | 0 | 0 | 0 | 0 | 0 | F2N1 | F2 | |
| 4002 | 0 | | F1 | 0 | 0 | 0 | 0 | F1 | 0 | F1 | F1 | F1 | |
| 4003 | 0 | 0 | F2 | 0 | 0 | 0 | 0 | 0 | 0 | 0 | F3G3 | 0 | |
| 4004 | F1G1 | F1 | F2G1 | F2G2 | F1G1 | N4 | F2G1 | F3G1 | F1 | F1G1 | F3G2 | F3G3 | |
| 4051 | F3G2 | F2G1 | F3G3 | F3G3 | F2G1 | F3G1 | F3G2 | F3G3 | 0 | F3G2 | F3G2 | F3G3 | Increases fruit set |
| 4088 | 0 | 0 | 0 | 0 | 0 | F1 | 0 | F1 | 0 | 0 | F1 | F1 | |
| 4089 | 0 | 0 | 0 | 0 | 0 | F1 | F1 | F1G1 | F1 | F1G1 | E3G3 | 0 | |
| 4090 | 0 | F1 | F2 | F1 | F1 | F1 | F2G2 | F2G1 | F1G1 | F2 | N4 | F3 | Increases fruit set and tillering |
| 4091 | 0 | F1 | F2 | 0 | F1 | F1 | F1 | F2G1 | F1 | F1 | F2 | F3 | Increases fruit set |
| 4092 | 0 | F1 | F2 | 0 | F1 | F1 | F2G2 | F3G1 | G1 | F1 | F3G1 | F1 | Increases fruit set |
| 4093 | 0 | F2 | F3G1 | F2 | F1 | F3G2 | F1G1 | F3G2 | F1G2 | F2G1 | F3G2 | F3 | Increases fruit set and tillering |
| 4094 | 0 | 0 | F2 | 0 | F1 | F2G2 | 0 | F2 | F1 | F1 | F2N1 | F2 | |
| 4095 | G1 | F1 | F2G1 | 0 | F2G2 | F2G1 | F1G1 | F3G2 | F2G2 | F2G1 | F3G1 | F3G1 | Increases tillering, dark green color |
| 4098 | 0 | 0 | 0 | 0 | F1 | F2 | 0 | 0 | 0 | 0 | F2N2 | N1G1 | |
| 4106 | 0 | N3G2 | F1 | F1 | N3G2 | F2G1 | G2N1 | 0 | 0 | 0 | F3G3 | F1 | Increases tillering |
| 4146 | 0 | N2G1 | F1 | F1G1 | N1G1 | N4 | 0 | 0 | 0 | 0 | F1 | F3 | Increases fruit set |
| 4147 | 0 | N4 | N3G3 | 0 | N3G3 | N4 | 0 | — | 0 | — | F2 | 0 | |
| 4148 | 0 | N3G3 | N3G2 | 0 | N4 | N4 | — | F2 | — | 0 | 0 | F1 | |
| 4149 | 0 | 0 | F1 | 0 | 0 | 0 | F1 | F1G1 | F1G1 | 0 | 0 | 0 | |
| 4154 | 0 | 0 | F2G1 | F1 | F2G2 | F1 | F2G2 | F1G1 | F1 | F1G1 | F2 | F1 | |
| 4155 | G1 | F2 | F3G2 | F2G2 | F2G2 | F1 | F2G2 | F1G1 | F1 | F2 | F3G1 | F2 | Increases fruit set |
| 4156 | F1G1 | F1G1 | F3G2 | F3G2 | F2G2 | F3G2 | F2G1 | F2G1 | F1 | F2G2 | F2 | F2G1 | Increases fruit set |
| 4157 | F2G2 | F2 | F3G2 | F2G2 | F3G3 | F2G2 | F2G1 | F1 | F1 | F2G2 | F2 | F3 | Increases fruit set |
| 4162 | F1G1 | F2G1 | F3G1 | F3G1 | F2G1 | F2G2 | F2G1 | F1 | F1 | F2G2 | F1G1 | F3 | |
| 4163 | F3G3 | F2G2 | F3G3 | F1 | F2G2 | F3G1 | F2G1 | F1G2 | N1 | F2G1 | F3G3 | F3 | Increases fruit set and tillering |
| 4164 | F1 | N4 | F2G1 | F1 | F1 | F1G1 | F2G2 | F3E2 | 0 | 0 | F3G1 | N1F1 | Increases fruit set |
| 4165 | F2 | N4 | F3G1 | F2G1 | N2 | F2G2 | F2G1 | F3G2 | 0 | 0 | F2N2 | F3 | " |
| 4166 | F1 | N3G2 | F3G1 | F2 | F1 | F3G1 | F1 | 0 | F1 | 0 | F3G1 | F1 | Increases axillary growth |
| 4167 | F1 | N2G1 | F3G1 | F1 | N2 | F1 | F2G2 | F3G1 | 0 | 0 | F2 | F3 | Increases fruit set |
| 4168 | F2G2 | N4 | F2G1 | F2G1 | N2G2 | N3G3 | F2G2 | F1 | 0 | F1 | F2 | F2 | |
| 4169 | 0 | N3G3 | F3G2 | F1 | F2G1 | F2G2 | F1 | F1 | F1 | F1 | F3G3 | F3 | |
| 4170 | F2G1 | 0 | F2G1 | F2 | F3G3 | F3G1 | F2G1 | F1 | 0 | F1 | F2G1 | F1 | Increases fruit set |
| 4225 | F3G2 | F3G2 | F3G1 | F3G2 | F3G3 | F3G2 | F2G1 | F1 | 0 | F1 | F1 | F1 | " |
| 4226 | F2G2 | F3G2 | F3G2 | F3G2 | F2G2 | F2G2 | F2G1 | | F1 | F1 | F3G1 | F3G1 | Increases fruit set and tillering |
| 4227 | F1G1 | F1 | F2 | F3G2 | F2G1 | F3G2 | F2 | | F2G1 | F1N1 | F1 | | |
| 4228 | 0 | 0 | F1 | 0 | 0 | 0 | | | | | | | |

The use of many of the growth regulant compounds may be demonstrated by treatment of soybeans (*soja max*) to increase the number of seed pods and by treating tomato plants (*Lycopersicum esculentum*) to increase fruit set. In an illustrative experiment, *Soja max* (Evans variety) and *Lycopersicum esculentum* (Tiny Tim variety) were grown in 4-inch pots (one plant per pot) filled with greenhouse potting soil (2 parts good top soil, 1½ parts builders sand, 1½ parts peat, fertilized with 5 lb. of 12-12-6 fertilizer and 5 lb. of finely ground limestone per cu. yd.). Aqueous spray formulations were prepared and the potted plants were sprayed at a spray volume of 40 gal. per acre and at application rates of 16, 4, 1 and ¼ oz. per acre. The spray mixtures were prepared by dissolving the proper amount of growth regulant compound in 15 ml. of acetone, adding 2 ml. of a solvent-emulsifier mixture consisting of 60 wt. percent of a commercial polyoxyethylated vegetable oil emulsifier (96 wt. percent active ingredient, Emulphor EL-719), 20 wt. percent xylene and 20 wt. percent deodorized kerosene, then bringing total volume up to 80 ml by addition of a 0.156 wt. percent aqueous solution of liquid non-ionic dispersant (90 wt. percent active trimethylnonyl polyethylene glycol ether, Tergitol TMN-10). Two replicates were sprayed at all application rates. For comparative purposes, plants were also sprayed at 40 gal./acre with water. The number of seed pods and of fruit as percentage of arithmetic mean of the numbers on untreated plants was observed within approximately three weeks after spray treatment and the results are tabulated below. The extent of growth regulatory effect on the plants was estimated on a scale of 0 to 10 and is also recorded in the following table:

| GROWTH REGULATING EFFECTS ON TWO SPECIES | | | | |
|---|---|---|---|---|
| | *Soja mar* | | | |
| | Pod Count[1] Percent in | | *Lycopersicum esculentum* | |
| | Comparison | Growth | Fruit Count[1] Percent in | Growth |
| Compound No. | Rate (oz/A) | to Untreated Plants | Regulating Effect[2] | Comparison to Untreated Plants | Regulating Effect[2] |
| 3595 | 16 | 147 | 8.5 | 171 | 5 |
| | 4 | 140 | 3 | 186 | 2.5 |
| | 1 | 124 | 1.5 | 186 | 0 |
| 3600 | 16 | 104 | 2.5 | 150 | 9 |
| | 4 | 101 | 1 | 525 | 2 |
| | 1 | 115 | 0 | 150 | 0 |
| 3779 | 16 | 138 | 4.5 | 147 | 3.5 |
| | 4 | 121 | 1.5 | 74 | 0.5 |
| | 1 | 121 | 1 | 59 | 0 |
| 3817 | 16 | 133 | 2 | 206 | 1 |
| | 4 | 108 | 0.5 | 74 | 0 |
| | 1 | 100 | 0 | 59 | 0 |
| 3818 | 16 | 104 | 2.5 | 132 | 0.5 |
| | 4 | 104 | 1 | 132 | 0 |
| | 1 | 100 | 0.5 | 88 | 0 |
| 3848 | 16 | 146 | 6 | 176 | 1.5 |
| | 4 | 113 | 2.5 | 162 | 1.5 |
| | 1 | 100 | 0.5 | 118 | 0 |

[1]Check = 100
[2]Greenhouse rating on scale of 0, no effect; 10, total kill.

The information presented in tabular form herein will enable a worker in the art to make a selection from among the growth regulant compounds of the invention and to make some judgment with regard to application rates, depending upon the effect which is desired. It may be seen, for example, that total kills of some species of vegetation may occur at application rates as high as 5 to 10 lb. per acre, whereas beneficial effects may be observed on living plants at application rates of 1 lb. per acre or less.

The growth regulant compounds are usually applied in combination with inert carriers or diluents, as in aqueous sprays, granules and dust formulations in accordance with established practice in the art. An aqueous spray is usually prepared by mixing a wettable powder or emulsifiable concentrate formulation of a growth regulant with a relatively large amount of water to form a dispersion.

Wettable powders comprise intimate, finely divided mixtures of growth regulant compounds, inert solid carriers and surface active agents. The inert solid carrier is usually chosen from among the attapulgite clays, the kaolin clays, the montmorillonite clays, the diatomaceous earths, finely divided silica and purified silicates. Effective surfactants, which have wetting, penetrating and dispersing ability are usually present in a wettable powder formulation in proportions of from 0.5 to about 10 percent by weight. Among the surface active agents commonly used for this purpose are the sulfonated lignins, naphthalenesulfonates and condensed naphthalenesulfonates, alkylbenzenesulfonates, alkyl sulfates and non-ionic surfactants such as products of condensation of ethylene oxide with alkylphenols.

Emulsifiable concentrates of the growth regulant compounds comprise in each instance, a solution of growth regulant compound in a liquid carrier which is a mixture of water-immiscible solvent and surfactants, including emulsifiers. Useful solvents include aromatic hydrocarbon solvents such as the xylenes, alkylnaphthalenes, petroleum distillates, terpene solvents, ether-alcohols and organic ester solvents. Suitable emulsifiers, dispersing and wetting agents may be selected from the same classes of products which are employed in formulating wettable powders.

In general, the growth regulants are seldom applied without the presence of a carrier or surfactant. However, direct application to plant seeds prior to planting may be accomplished in some instances by mixing powdered solid growth regulant with seed to obtain a substantially uniform coating which is very thin and comprises only one or two percent by weight or less, based on the weight of the seed. In most instances, however, a non-phytotoxic solvent, such as methanol is employed as a carrier to facilitate the uniform distribution of growth regulant on the surface of the seed.

When a compound is to be applied to the soil, as for a pre-emergence application, granular formulations are sometimes more convenient than sprays. A typical granular formation comprises the growth regulant compound dispersed on an inert carrier such as coarsely ground clay, or clay which has been converted to granules by treatment of a rolling bed of the powdered material with a small amount of liquid in a granulating drum. In the usual process for preparing granular formulations, a solution of the active compound is sprayed on the granules while they are being agitated in a suitable mixing apparatus, after which the granules are dried with a current of air during continued agitation.

We claim:

1. The method of regulating the growth of plants, including combating unwanted vegetation, comprises applying to the plants, either on seed, the soil or directly on the plants an effective amount of a compound having the general structural formula:

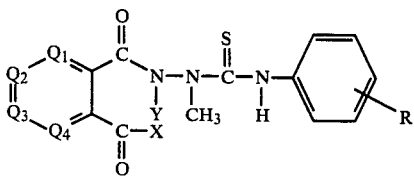

in which

Q₁, Q₂, Q₃ or Q₄ is N,

X is —OH or —O—(C₁-C₄ alkyl) and Y is H or X and Y together represent a bond between carbon and nitrogen atoms and R is H or one or two of the following substituents: —Br, —Cl, —F, —I, —CF₃, —CH₃, —NO₂ or —C≡N or an agriculturally acceptable salt thereof.

2. The method according to claim 1 in which Q₁ is N, X is —OH and Y and R are both —H.

3. The method according to claim 1 in which Q₃ is N, X is —OH and Y and R are both —H.

4. The method according to claim 1 in which Q₄ is N, X is —OCH₃, Y is —H and R is 4-fluoro.

5. The method according to claim 1 in which Q₂ is N, X is —OCH₃ and Y and R are both —H.

6. The method according to claim 1 in which Q₂ is N, X and Y together form a C—N bond and R is —H.

7. The method according to claim 1 in which Q₁ is N, X is —OH, Y is —H and R is 3-chloro-2-methyl.

8. The method according to claim 1 in which Q₁ is N, X is —OH, Y is —H and R is 4-fluoro.

9. The method according to claim 1 in which Q₁ is N, X is —OH, Y is —H and R is 3,5-dichloro.

10. The method according to claim 1 in which Q₁ is N, X is —OH, Y is —H and R is 3-trifluoromethyl.

11. The method according to claim 1 in which Q₁ is N, X is —OH, Y is —H and R is 4-methyl.

12. The method according to claim 1 in which Q₁ is N, X is —OH, Y is —H and R is 3-chloro.

13. The method according to claim 1 in which Q₁ is N, X is —OH, Y is —H and R is 3,4-dimethyl.

14. The method according to claim 1 in which Q₁ is N, X is —OH, Y is —H and R is 2,4-dimethyl.

15. The method according to claim 1 in which Q₁ is N, X is —OH, Y is —H and R is 3-methyl.

16. The method according to claim 1 in which Q₁ is N, X is —OH, Y is —H and R is 3,4-dichloro.

17. The method according to claim 1 in which Q₁ is N, X is —OH, Y is —H and R is 4-chloro.

18. The method according to claim 1 in which Q₄ is N, X is —OCH₃, Y is —H and R is 3-methyl.

19. The method according to claim 1 in which Q₄ is N, X is —OCH₃, Y is —H and R is 3,4-dichloro.

20. The method according to claim 1 in which Q₄ is N, X is —OCH₃, Y is —H and R is 3,5-dichloro.

21. The method according to claim 1 in which Q₄ is N, X is —OCH₃, Y is —H and R is 3-trifluoromethyl.

22. The method according to claim 1 in which Q₄ is N, X is —OCH₃, Y is —H and R is 3-chloro.

23. The method according to claim 1 in which Q₁ is N, X and Y form a C—N bond and R is 4-fluoro.

24. The method according to claim 1 in which Q₁ is N, X and Y form a C—N bond and R is 2-chloro.

25. The method according to claim 1 in which Q₁ is N, X and Y form a C—N bond and R is 3-chloro-2-methyl.

26. The method according to claim 1 in which Q₁ is N, X and Y form a C—N bond and R is 4-nitro.

27. The method according to claim 1 in which Q₁ is N, X and Y form a C—N bond and R is —H.

28. The method according to claim 1 in which Q₁ is N, X and Y form a C—N bond and R is 3-trifluoromethyl.

29. The method according to claim 1 in which Q₁ is N, X and Y form a C—N bond and R is 4-methyl.

30. The method according to claim 1 in which Q₁ is N, X and Y form a C—N bond and R is 3-chloro.

31. The method according to claim 1 in which Q₁ is N, X and Y form a C—N bond and R is 3,4-dimethyl.

32. The method according to claim 1 in which Q₁ is N, X and Y together form a C—N bond and R is 3-methyl.

33. The method according to claim 1 in which Q₁ is N, X and Y together form a C—N bond and R is 3,4-dichloro.

34. The method according to claim 1 in which Q₁ is N, X is —OH, Y is —H and R is 3-bromo.

35. The method according to claim 1 in which Q₁ is N, X is —OH, Y is —H and R is 4-methyl.

36. The method according to claim 1 in which Q₁ is N, X is —OH, Y is —H and R is 2-fluoro.

37. The method according to claim 1 in which Q₁ is N, X and Y together form a C—N bond and R is 3-bromo.

38. The method according to claim 1 in which Q₁ is N, X and Y together form a C—N bond and R is 4-trifluoromethyl.

39. The method according to claim 1 in which Q₁ is N, X and Y together form a C—N bond and R is 2-fluoro.

40. The method according to claim 1 in which Q₁ is N, X is —OH, Y is —H and R is 4-iodo.

41. The method according to claim 1 in which Q₁ is N, X is —OH, Y is —H and R is 4-bromo.

42. The method according to claim 1 in which Q₁ is N, X is —OH, Y is —H and R is 2,4-dichloro.

* * * * *